US010961558B2

(12) United States Patent
Choi et al.

(10) Patent No.: US 10,961,558 B2
(45) Date of Patent: Mar. 30, 2021

(54) SUBSTANCE OR CONTAMINATION DETECTION

(71) Applicant: VERITIDE LIMITED, Christchurch (NZ)

(72) Inventors: Joon Koo Choi, Christchurch (NZ); Craig Simon Tuffnell, Huntsbury (NZ); James Martin Boulton, Christchurch (NZ)

(73) Assignee: VERITIDE LIMITED, Christchurch (NZ)

(*) Notice: Subject to any disclaimer, the term of this patent is extended or adjusted under 35 U.S.C. 154(b) by 0 days.

(21) Appl. No.: 16/819,954

(22) Filed: Mar. 16, 2020

(65) Prior Publication Data

US 2020/0392555 A1 Dec. 17, 2020

Related U.S. Application Data

(63) Continuation of application No. 15/125,618, filed as application No. PCT/NZ2015/050026 on Mar. 13, 2015, now abandoned.

(30) Foreign Application Priority Data

Mar. 14, 2014 (NZ) ........................ 622444

(51) Int. Cl.
| G01N 33/12 | (2006.01) |
| G01N 21/64 | (2006.01) |
| G01J 3/44 | (2006.01) |
| G01N 21/94 | (2006.01) |
| C12Q 1/04 | (2006.01) |
| G06K 9/00 | (2006.01) |

(52) U.S. Cl.
CPC .............. *C12Q 1/04* (2013.01); *G01J 3/4406* (2013.01); *G01N 21/6456* (2013.01); *G01N 21/94* (2013.01); *G01N 33/12* (2013.01); *G06K 9/00134* (2013.01); *G01J 3/44* (2013.01)

(58) Field of Classification Search
CPC . C12Q 1/04; G01J 3/4406; G01J 3/44; G01N 21/6456; G01N 21/94; G01N 33/12; G06K 9/00134
See application file for complete search history.

(56) References Cited

U.S. PATENT DOCUMENTS

| 5,621,215 | A | * | 4/1997 | Waldroup ............ A22B 5/0064 250/359.1 |
| 5,658,798 | A |  | 8/1997 | Bertin et al. |
| 5,821,546 | A |  | 10/1998 | Xiao et al. |
| 5,914,247 | A | * | 6/1999 | Casey .................... G01N 21/64 356/317 |
| 6,587,575 | B1 | * | 7/2003 | Windham ............... G01N 33/12 382/110 |
| 6,639,665 | B2 | * | 10/2003 | Poole ...................... G01N 21/31 209/576 |

(Continued)

FOREIGN PATENT DOCUMENTS

| EP | 2270475 A1 | 1/2011 |
| EP | 2525213 A1 | 11/2012 |

*Primary Examiner* — Christine S. Kim

(74) *Attorney, Agent, or Firm* — Dann, Dorfman, Herrell and Skillman, P.C.

(57) ABSTRACT

A spectroscopic method and system detects the amount of one or more substances or contaminants in or on a product, such as fecal contamination on meat samples.

11 Claims, 5 Drawing Sheets

(56) References Cited

U.S. PATENT DOCUMENTS

| | | |
|---|---|---|
| 7,209,836 B1 | 4/2007 | Schermer et al. |
| 7,547,508 B1 | 6/2009 | Lefcourt et al. |
| 2003/0164456 A1 | 9/2003 | Petrich et al. |
| 2006/0008866 A1* | 1/2006 | Flick ............... G01N 21/6486 435/34 |
| 2011/0117025 A1* | 5/2011 | Dacosta ........... G01N 21/6456 424/9.6 |
| 2012/0223251 A1 | 9/2012 | Morrow et al. |
| 2012/0280146 A1 | 11/2012 | Rizkallah et al. |
| 2015/0330898 A1* | 11/2015 | Choi ....................... C12Q 1/04 435/34 |
| 2016/0109423 A1* | 4/2016 | Reichl ............... G01N 21/6486 250/459.1 |

\* cited by examiner

SUBSTANCE OR CONTAMINATION DETECTION

REFERENCE TO PRIOR APPLICATION

This application is a continuation of U.S. application Ser. No. 15/125,618, which was the National Stage of International Application PCT/NZ2015/050026, filed on Mar. 13, 2015, the entireties of which are incorporated herein by reference.

FIELD OF THE INVENTION

The invention relates to real time detection of substances or contaminants, and in particular to a spectroscopic method, system and device for detection of fecal contamination on meat samples.

BACKGROUND OF THE INVENTION

Animal feces contain microbial pathogens such as *Escherichia coli* 0157:H7, *Campylobacter* and *Salmonella* and it also caters for bacteria growth. During the slaughtering process, carcasses can be contaminated with fecal residue when intestinal tracks and pelts are removed. After the slaughtering process each carcass is visually inspected and intervened upon positive detection of fecal contamination and/or upon detection of other contaminations. However, given the rapid nature of processing plants some contaminated carcasses may proceed to further processing without being detected. This may result in cross contaminations. At such point in time, the traceability of contaminated products diminishes, meaning large scale recall is unavoidable upon positive fecal detection.

Some government authorities mandate meat processors to water wash every carcass to reduce visual incident of fecal residue. The effect of water wash not only visually removes fecal residue but also dilutes and distributes fecal material on carcasses. Visual inspections are often subjective, insensitive and require training. Visual inspections are an inefficient means for detecting diluted fecal residue on carcasses.

In grass-fed animals, chlorophyll and its metabolites are largely present in feces. Also chlorophyll can be found in feces from grain-fed bovines. Spectroscopic techniques for determining the presence of chlorophyll and its metabolites in feces are known. In such devices, a sample is typically exposed to a light signal having a certain excitation wavelength, and a light detector detects emitted light of a longer wavelength (fluorescence) from the sample to identify the presence of bacteria. Spectroscopy is often real time, non invasive, non-destructive and non-chemical. Through careful examinations of excitation and emission spectra of chlorophyll one can construct 'fingerprints' for fecal detection and identification.

A spectroscopic detection method is disclosed in U.S. Pat. No. 5,914,247 for example.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

It is an object of the present invention to provide an alternative spectroscopic method, system or device for detection of one or more substances or contaminants, such as fecal contaminations on a meat sample, or to at least provide the public with a useful choice.

SUMMARY OF THE INVENTION

In a first aspect the invention may broadly be said to consist of a method for determining the amount of one or more substances or contaminants in or on an illuminated product, the method comprising the steps of:
  receiving a first signal indicative of intensity of light emitted from the product across a first waveband,
  receiving a second signal indicative of intensity of light emitted from the product across a second waveband containing one or more wavelengths associated with the fluorescent properties of the contaminants or substances to be detected,
  determining or predicting a value indicative of an amount of the substance or contaminant, for each of, or at least one of, the one or more substances or contaminants in or on the product, from the first and second signals and from predetermined information relating to fluorescence behaviour of a same or similar product or a main or more abundant substance of the product isolated from the substance or contaminant (hereinafter referred to as isolated product) and/or relating to the fluorescence behaviour of the substance or contaminant isolated from the product.

Preferably the second waveband is within the first waveband. Alternatively the second waveband may be outside the first waveband.

Preferably the step of determining or predicting the value indicative of the amount of the substance or contaminant comprises separating from the first signal a portion of the signal relating to the substance or contaminant based on: the second signal, the fluorescent behaviour of the substance or contaminant in isolation from the product and the fluorescent behaviour of the isolated product.

Preferably the method further comprises determining or predicting a value indicative of an amount of the main or more abundant substance of the product by separating from the first signal a portion of the signal relating to the main substance based on: the second signal, the fluorescent behaviour of each isolated substance or contaminant and the fluorescent behaviour of the isolated product.

Preferably the predetermined information relates to:
  first and second isolated product signals indicative of the light emitted from the isolated (uncontaminated) product across the first and second wavebands respectively in response to optical excitation, and
  for each of the one or more isolated substances or contaminants, first and second isolated substance or contaminant signals indicative of the light emitted from the isolated substance or contaminant within the first and second wavebands respectively in response to optical excitation.

Preferably the predetermined information is indicative of: a strength of each of the first and second isolated product signals and for each of the one or more isolated substances or contaminants, a strength of each the first and second isolated substance or contaminant signals.

Preferably the strength of the isolated product signal is an integral of an intensity of the isolated product signal across the relevant waveband, and the strength of the isolated substance or contaminant signal is an integral of an intensity of the isolated substance or contaminant signal across the relevant waveband.

Preferably the predetermined information includes one or more of:
- a normalised strength of the first and/or second isolated product signal relative to the first isolated product signal, and
- a normalised strength of the first and/or second isolated substance or contaminant signal relative to the first isolated substance or contaminant signal, for each of the isolated substances or contaminants.

In one embodiment the step of determining or predicting the value indicative of the amount of the substance or contaminant comprises multiplying the first and second signals by the inverse of a matrix, A, containing the strength of each of the first and second isolated product signals and the strength of each the first and second isolated substance or contaminant signals, for each of substance or contaminants.

A may be an n by n or m by n sized matrix, where n and m depend on the number of substances or contaminants to be determined.

Preferably the entries of matrix A relating to the isolated product are normalised to the strength of the first isolated product signal and for each contaminant or substance, the entries relating to the substance or contaminant are normalised to the strength of the first isolated substance or contaminant signal.

For example, for determining of the value of the amount of one substance or contaminant, the matrix A is:

$$A = \begin{bmatrix} \left(\frac{Det1}{Det1}\right)_{IP} & \left(\frac{Det1}{Det1}\right)_{C} \\ \left(\frac{Det2}{Det1}\right)_{IP} & \left(\frac{Det2}{Det1}\right)_{C} \end{bmatrix} = \begin{bmatrix} 1 & 1 \\ E_{IP} & E_{C} \end{bmatrix} \text{ and}$$

$$A^{-1} \times \begin{bmatrix} Det1_P \\ Det2_P \end{bmatrix} = \begin{bmatrix} I_P \\ I_C \end{bmatrix}$$

wherein
$Det1_{IP}$=the strength of the first isolated product signal,
$Det2_{IP}$=the strength of the second isolated product signal,
$Det1_c$=the strength of the first isolated substance or contaminant signal,
$Det2_c$=the strength of the second isolated substance or contaminant signal,
$Det1_P$=the strength of the first product signal,
$Det2_P$=the strength of the second product signal,
$I_P$=a value indicative of the amount of the product, and
$I_C$=a value indicative of the amount of the substance or contaminant in or on the product.

In an alternative embodiment the step of determined or predicting the value indicative of the amount of the substance or contaminant comprises determining a parameter, $R_C$, indicative of the deviation of the signals associated with the product from the signals associated with the isolated product.

Preferably $$R_C = \left(\left(\frac{Det2}{Det1}\right)_P - \left(\frac{Det2}{Det1}\right)_{IP}\right) \times Det2_P$$

wherein:
$Det1_P$=the strength of the first product signal,
$Det2_P$=the strength of the second product signal,
$Det1_{IP}$=the strength of the first isolated product signal, and
$Det2_{IP}$=the strength of the second isolated product signal.

Preferably the method further comprises prior to receiving the first and second signals, the steps of:
- illuminating the product with light at an excitation wavelength outside the first and second wavebands,
- receiving light emitted from the product in response to the illumination, and
- filtering the emitted light into first and second filtered light signals within the first and second wavebands respectively.

Preferably the method further comprises prior to receiving the first and second signals, the step of deriving the predetermined information.

Preferably the step of deriving the predetermined information comprises:
- obtaining the first and second isolated product signals,
- obtaining for each of the substances or contaminants, the first and second isolated substance or contaminant signal.

Preferably obtaining the first and second isolated product signals comprises:
- illuminating the isolated product with light at the excitation wavelength outside the first and second wavebands,
- receiving light emitted from the product in response to the illumination, and
- filtering the emitted light into first and second filtered light signals within the first and second wavebands respectively.

Preferably obtaining the first and second isolated substance or contaminant signals comprises:
- illuminating the isolated substance or contaminant with light at the excitation wavelength outside the first and second wavebands,
- receiving light emitted from the substance or contaminant in response to the illumination, and
- filtering the emitted light into first and second filtered light signals within the first and second wavebands respectively.

The product may be a meat sample or carcass, the main or more abundant substance of the product may be any combination of one or more of collagen, tissue or fat and the substance(s) or contaminant(s) to be determined may be any combination of one or more of: fecal residue, fat, porphyrin, collagen or bacteria.

Preferably the excitation wavelength is between approximately 350 nm to 650 nm. More preferably the excitation wavelength is approximately 365 nm, 405 nm, 450 nm, 532 nm or 650 nm. Most preferably the excitation wavelength is 450 nm.

Preferably the first waveband is between approximately 625 nm and 850 nm.

Preferably the second waveband is between approximately 666 nm and 676 nm.

Preferably the first waveband is approximately 450-800 nm and the second waveband is approximately 580-800 nm.

Preferably the excitation light is frequency modulated to between 1 kHz and 10 MHz.

In a second aspect the invention may broadly be said to consist of a method for determining or predicting the amount of one or more substances or contaminants in or on an illuminated product, the method comprising the steps of:
- receiving at least one signal indicative of intensity of light emitted from the product across a waveband, and
- determining or predicting the amount of each, or at least one, of the one or more substances or contaminants in or on the product by separating a portion of the emitted signal relating to the substance or contaminant from the overall signal emitted from the product based on fluorescent behaviour of the substance or contaminant in isolation from the product and/or based on the fluorescent behaviour of the product or a main or more abundant substance of the product in isolation from the substances or contaminants (hereinafter referred to as isolated product).

Preferably the step of receiving at least one signal comprises:
 receiving a first signal indicative of intensity of light emitted from the product across a first waveband,
 receiving a second signal indicative of intensity of light emitted from the product across a second waveband and containing one or more wavelengths associated with the fluorescent properties of the contaminants or substances to be detected, Preferably the second waveband is within the first waveband. Alternatively the second waveband may be outside the first waveband.

Preferably the step of determining or predicting the value indicative of the amount of the substance or contaminant comprises separating from the first signal a portion of the signal relating to the substance or contaminant based on: the second signal, the fluorescent behaviour of the substance or contaminant in isolation from the product and the fluorescent behaviour of the isolated product.

Preferably the method further comprises determining or predicting a value indicative of an amount of the main or more abundant substance of the product by separating from the first signal a portion of the signal relating to the main substance based on: the second signal, the fluorescent behaviour of each isolated substance or contaminant and the fluorescent behaviour of the isolated product.

In a third aspect the invention may broadly be said to consist of a method for determining fecal contamination in a product comprising the steps of:
 determining the amount of a contaminant in or on the product in accordance with the method of either the first or second aspect of the invention, and
 determining fecal contamination when the amount of the contaminant exceeds a predetermined threshold or thresholds.

Preferably the method further comprises outputting a signal indicative of fecal contamination when the amount of the contaminant exceeds the predetermined threshold or thresholds.

The amount may be determined based on either $I_c$, $R_c$ or a combination of both.

The step of determining fecal contamination may include determining contamination when $I_C$ exceeds a predetermined I threshold, when $R_C$ exceeds a predetermined R threshold, or when both $I_C$ and $R_C$ exceed both the I threshold and the R threshold respectively.

In a fourth aspect the invention may broadly be said to consist of a device for determining an amount of one or more substances or contaminations in or on a product, the device comprising:
 a memory component for storing data indicative of predetermined information relating to fluorescence behaviour of a same or similar product or a main or more abundant substance of the product isolated from a substance or contaminant (hereinafter referred to as isolated product) and/or relating to the fluorescence behaviour of each of the one or more substances or contaminants isolated from the product, and
 a processor configured to:
  receive a first signal indicative of intensity of light emitted from the product across a first waveband,
  receive a second signal indicative of intensity of light emitted from the product across a second waveband and containing one or more wavelengths associated with the fluorescent properties of the contaminants or substances to be detected,
  determine or predict a value indicative of an amount of each, or at least one, of the substance or contaminant, in or on the product from the first and second signals and from the predetermined information.

Preferably the second waveband is within the first waveband. Alternatively the second waveband may be outside the first waveband.

Preferably the device further comprises a light source for generating a beam of light.

In one embodiment the device further comprises:
 a first band pass filter arranged to filter a light beam and having a first operative waveband associated with the first waveband, and
 a second band pass filter arranged to filter a light beam and having a second operative waveband associated with the second waveband.

Preferably the device further comprises first and second photomultiplier tubes adjacent the first and second filters respectively, for receiving filtered light beams from the first and second filters and outputting the first and second signals indicative of light intensities to the processor respectively.

Preferably the device further comprises an optical fibre cable coupled to the light source for transmitting light out of the device and onto the product and for transmitted light emitted from the product to the first and second filters.

Preferably the cable is optically coupled to a lens element adjacent the product.

Preferably the lens is arranged to yield an excitation light beam from a central excitation fibre of the fibre cable onto a region of interest on the product in one direction and yield an emission light beam emitted from the product into emission fibres of the fibre cable in an opposite direction.

In an alternative embodiment the device further comprises a camera lens configured to receive light emitted from the product in response to excitation from the light source and output an image signal.

Preferably the device further comprises a beam splitter configured to divide the image signal into a first and second channel.

Preferably the device further comprises a first image sensor with a first optical filter associated with the first channel and a second image sensor with a second optical filter associated with the second channel, wherein a first optical filter is arranged to filter the output image signal based on a first operative waveband, and the second optical filter is arranged to filter the output image signal based on a second operative waveband, the second waveband being within the first waveband.

In a fifth aspect the invention may broadly be said to consist of a system for determining an amount of one or more substances or contaminations in or on a product, the system comprising:
 a light source for illuminating the product with excitation light, and
 a light detector for determining the amount of one or more substances or contaminations in or on a product, the detector having:
  a memory component for storing data indicative of predetermined information relating to fluorescence behaviour of a same or similar product or a main or more abundant substance of the product isolated from a substance or contaminant (hereinafter referred to as isolated product) and/or relating to the fluorescence behaviour of each of the one or more substances or contaminants isolated from the product, and a processor configured to:

receive a first signal indicative of intensity of light emitted from the product across a first waveband, receive a second signal indicative of intensity of light emitted from the product across a second waveband and containing one or more wavelengths associated with the fluorescent properties of the contaminants or substances to be detected, determine or predict a value indicative of an amount of each, or at least one, of the substance or contaminant, in or on the product from the first and second signals and from the predetermined information.

Preferably the second waveband is within the first waveband. Alternatively the second waveband may be outside the first waveband.

It will be appreciated any one or more of the above aspects can be provided in combination with any one or more of the above preferred or alternative embodiments or features.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

The invention consists in the foregoing and also envisages constructions of which the following gives examples only.

BRIEF DESCRIPTION OF THE DRAWINGS

Preferred embodiments of the invention will be described by way of example only and with reference to the drawings, in which.

DETAILED DESCRIPTION OF PREFERRED EMBODIMENTS

1. Overview of Detection System

Figure 1:
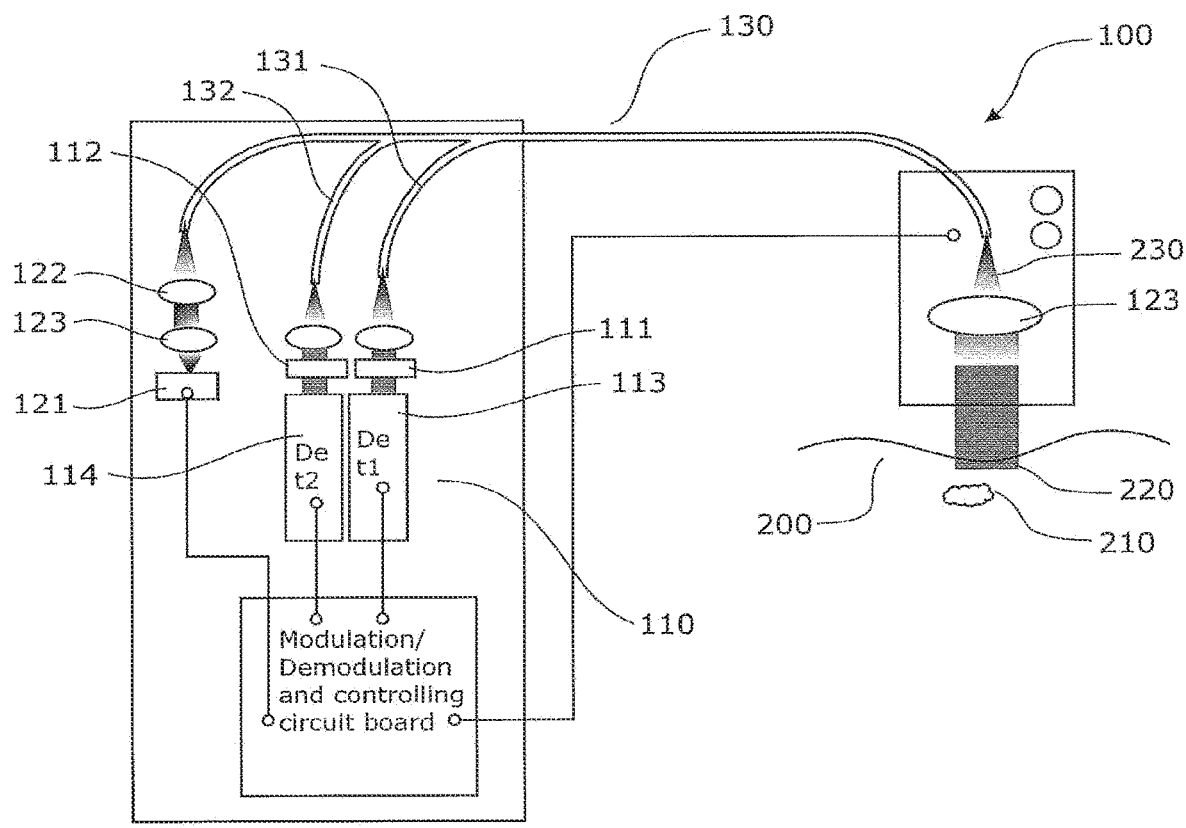
FIG. 1 is a schematic of showing the components of a preferred form detector of the invention.

Referring to FIG. 1, a schematic of a preferred form detection system 100 of the invention is shown. The system 100 comprises an illumination sub-system 120 and a detection sub-system 110 (hereinafter "detector" 110. The system 100 is spectroscopic and utilises the fluorescent properties of contaminants such as feces, or other substance(s) or matter, to identify the presence of one or more of said contaminants or other substances 210 within or on a target product or sample 200. The system 100 operates by illuminating the sample 200 using a light beam from a light source 121, and analysing at the detector 110 light emitted from the product 200 in response to the illumination. A light transmission medium 130 may provide optical communication between the light source and the product, and between the product and the detector. A product or sample 200 to be analysed is positioned adjacent the output of the illumination sub-system 120 to yield an excitation beam onto the area 220 of the product to be analysed.

The product 200 may be from a living or non-living species or surface. For example, as in the case of the preferred embodiments, the product is from a living species such as a meat product, a fruit product or a vegetable product. Alternatively the product 200 may be or may be from a non-living surface or structure such as a bench, tool, piece of equipment or any other non-living surface where the detection of a contaminant or other substance may be desirable.

The detector 110 is arranged to receive light emitted from the illuminated region 220 of the product 200 and analyse the emission spectra to determine the presence and preferably the absolute amount of each of one or more substances or contaminants. The detector 110, in particular, is arranged to separate from the emission spectra, the portion of the signal relating to the substance or contaminant and calculate an absolute amount of the contaminant or substance from this portion of the signal. The detector 110 may be further configured to determine if the absolute the amount exceeds a predetermined threshold and output a signal to a user accordingly to indicate as such.

To separate the portion of the emitted signal relating to the contaminant or substance from the remainder of the signal, an initial analysis stage is conducted where the fluorescence behaviour of a similar product in isolation of the contaminant or substance, and an analysis of the fluorescence behaviour of each contaminant or substance to be detected in isolation of the product is determined. The predetermined fluorescence behaviour information is stored in memory for processing at a later stage when a product is to be analysed for contamination or the detection of a substance/contaminant.

During product analysis, the emission signal from the product is analysed in conjunction with the predetermined information to determine the presence and preferably the absolute amount of each contaminant or substance to be detected. In particular, the emitted fluorescence or photoluminescence signal is filtered into two or more signals, including a base signal and one or more fluorescence signals. In the preferred embodiment, the base signal has a relatively wide waveband/bandwidth and includes, for each contaminant or substance to be detected, at least one of the fluorescence wavelength associated with that contaminant or substance. In alternative embodiments, the base signal may be a narrowband signal. The width of the waveband of the base signal depends on the spectral signatures of the contaminant or substance to be detected. The emitted fluorescence signal is also filtered into at least one fluorescence signal for each contaminant or substance to be detected. In the preferred embodiment, the waveband of each fluorescence signal contains a fluorescence wavelength of an associated contaminant or substance to be detected. Each fluorescence signal has a waveband that is different to the waveband of the base signal. The waveband of the fluorescence signal is preferably relatively narrow compared to the base signal. In the preferred embodiment, the fluorescence signal comprises a waveband that is contained entirely within the waveband of the base signal. In other words, the fluorescence signal forms part of the overall base signal. In alternative embodiments however, any one of the fluorescence signals may have a relatively wider or same width waveband as the base signal, and/or the waveband of the fluorescence signal may partially overlap with or be contained entirely outside the waveband of the base signal.

The base signal and each of the fluorescence signals are utilised and processed by the detector in conjunction with the predetermined information relating to the fluorescence behaviour of the isolated product and substances/contaminants to determine the presence of each contaminant or substance, and preferably the absolute amount of each contaminant or substance in or on the product.

The methods and systems described for this invention are not intended to be limited to any particular application. The preferred embodiment predominantly used to describe the features of the invention is for the detection of feces or other contaminants or substances or matter such as tissue or fat in or on meat products. However, it will be appreciated that the method and system for detection can be applied in various alternative applications to detect the presence, and preferably the absolute amount of any species or substance or matter on a product that exhibits fluorescent properties when the product is illuminated. Such alternative applications are not intended to be excluded from the scope of the invention.

In the preferred embodiment, the detector 110 is configured to operate in real time. The detector 110 is configured to receive, filter and process the light emitted from the illuminated region 220 of the product 200 in real time or near real time with minimal delay from time of excitation. Such a detector 110 can therefore be used in a multitude of applications where real time detection is necessary or highly beneficial such as in the food product industries where a large number of products may need to be examined for contamination and transported to another location quickly and efficiently.

1.1 Electronic System

Two embodiments of the hardware for the illumination 120 and detection 110 sub-systems are described below with reference to FIGS. 1 and 2. The first embodiment is more suited for portable or smaller type detection devices for analysing smaller products or portions of products, whereas the second embodiment may be more suited for analysing larger portions or larger products.

In both embodiments, the illumination system comprises a light source. The light source 120 is any device capable of producing light of one or more excitation wavelengths as required by the particular application. In the preferred embodiment, the light source 121 delivers (monochromatic) light of wavelengths between approximately 350 nm and 700 nm, and more preferably at excitation wavelengths of or around approximately 365 nm, 405 nm, 450 nm, 532 nm and 650 nm. In the preferred application of fecal detection, the light source 121 delivers an excitation light of approximately 450 nm as this is the optimum wavelength for maximizing the fluorescence ratio between chlorophyll (indicative of presence of feces) and meat background.

In both embodiments, the detector 110 is configured to receive the emitted fluorescence signal from the product in response to excitation and output one or more filtered signals for processing by the signal processing component, in particular a base signal and one or more fluorescence signals. In the preferred embodiment, the detector 110 is arranged for detection of the presence of fecal matter on the surface of a meat product 200. Chlorophylls and their metabolites are present in the fecal matter of plant eating animals and exhibit fluorescent properties when exited by light. Chlorophyll is therefore a suitable indicator for the inspection and identification of fecal contamination. Chlorophyll or the metabolites of Chlorophyll fluoresce with a spectral waveband of approximately 650-750 nm when excited by light having a wavelength between 350 nm and 650 nm. In the preferred embodiment, the detector 110 is configured to output a base signal having a waveband of approximately 625 nm to 850 nm and a fluorescence signal having a waveband of approximately 666 nm to 676 nm.

The signal processing component of the system is preferably integrated within the detector 110 of either embodiment but may alternatively be integrated in a separate and/or remote system. The same hardware can be, and is preferably, used for obtaining the predetermined fluorescence behaviour information which is utilised by the signal processing system to detect contaminations or other substances in or on a product.

1.1.1 First Embodiment

Referring to FIG. 1, in the first embodiment, the illumination sub-system 120 comprises a light source 121 and one or more lenses 122/123 for focussing the light onto the appropriate region or regions of the product.

The light source 121 may be, for example, a diode laser configured to output an excitation beam at the desired wavelength. The light source 121 may be housed within the detector 110 or alternatively separate from the detector 110.

In this embodiment, one or more, and preferably a pair, of collimating and focussing lenses 122 are provided between the light source 121 and the transmission medium 130 to couple the excitation light beam with the transmission medium 130. In alternative embodiments, the light source 121 may be embedded in a probe allowing direct excitation of the product 200 without the need for a transmission medium.

The mode of operation of the light source 121 can be continuous, modulated or pulsed. In a preferred embodiment, the excitation light is frequency modulated between 1 kHz and 10 MHz so that fluorescence is also modulated at that frequency. This allows ambient signals to be rejected during signal processing. Alternatively, excitation light modulation can be achieved using a mechanical chopper as is well known in the art.

A collimating lens 123 is provided adjacent the product 200 for provided a focussed light beam on a desired region of the product. The lens 123 may be a convex lens for example adapted to deliver collimated excitation light spots of 5 mm, 10 mm or 20 mm diameter or any other desired size on the product 200. Alternatively, more complex sizes and shapes may be generated by devices such as galvanometers, rod lenses or cylindrical lenses. The incident angle of the excitation light beam on the product 200 may be any desired angle but is preferably approximately orthogonal (90 degrees) to the surface of the product 200.

It will be appreciated that alternative light sources and excitation wavelengths may be used as required by the particular application. The light source 121 may be configured to output one or more excitation light beams.

The detector 110 is configured to receive light emitted from the illuminated region 220 of the product 200 and output two or more distinct filtered light signals for processing by the signal processor. The number of filtered light signals may be dependent on the number of contaminants or substances to be detected in or on the product.

In the first embodiment, shown in FIG. 1, light is transmitted by the system 100 using optical cable 130 having an emission light branch. The light branch splits into two or more channels depending on the number of wavebands the signal is to be separated into. In the preferred embodiment, the light branch splits into two channels 131 and 132. A beam splitter may also be used in this process to redirect the emitted light across two separate channels.

At the end of each channel 131/132 is an optical filter 111/112 having a particular optical characteristic. A first filter 111 is configured to output the base signal having the relatively wider waveband from the emitted light, and a second filter 112 is configured to output the fluorescence signal of relatively narrower waveband from the emitted light. It will be appreciated that any number of second filters 112 may be used depending on the number of contaminants or substances to be detected. In the preferred embodiment, the first filter 111 is configured to output a base signal having a waveband of approximately 625 nm to 850 nm, and the second filter 112 is configured to output a fluorescence signal of approximately 666 nm to 676 nm. Due to the narrow waveband of the second filter 112, the gain voltage associated with the output of the filter 112 may be set higher than that for filter 111.

It will be appreciated that for different contamination, substance, matter, product and/or applications different wavebands may be used for the filters 111 and 112 without departing from the scope of the invention.

Referring back to FIG. 1, the light transmitted from filters 111 and 112 is then input into two respective photomultiplier tubes (PMTs) 113 and 114 or photodiodes. The tubes 113/114 have the function of outputting electrical energy in response to input optical energy. In other words, PMTs 113 and 114 convert the received light beams transmitted from filters 111 and 112 into current or voltage signals. The PMTs may then process the current or voltage signals or output the signals for external processing.

Control circuitry may be used to control the operation of the various components associated with this embodiment.

In the first embodiment an optical transmission medium 130 is an optical fibre cable 130 is provided for optically coupling the detector 110 and the light source to the region of the product to be analysed.

The optical cable 130 may comprise a bundle of optical fibres. These fibres are configured to allow the cable to separately transmit excitation and emission beams. In particular, the preferred form cable 130 comprises a central excitation fibre element surround by an array of emission fibre elements. It will be appreciated that the number and distribution of the fibre elements within the cable 130 may be different in alternative embodiments. Excitation light from the light source 120 travels through the excitation fibre to the lens 123 where it is projected onto the region 220 to be analysed. Light emitted from the region is projected by the lens 123 into the surrounding array of fibre elements to then be transmitted through the cable 130 to the beam splitter 116 and/or the various channels before the appropriate filters 111 and 112 of the detector 110.

1.1.2 Second Embodiment

Figure 2:
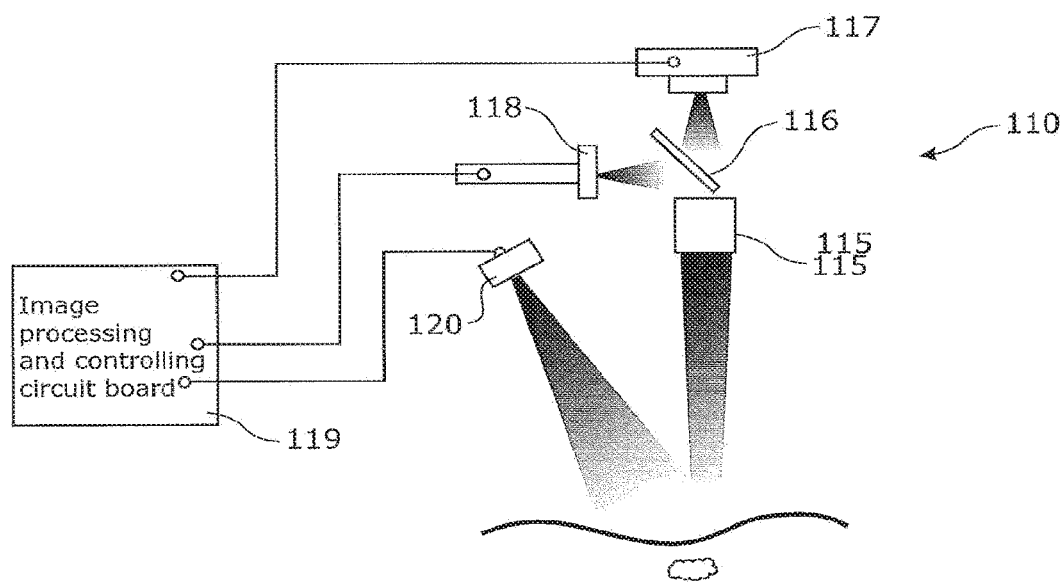
FIG. 2 is a schematic of showing the components of an imaging system of the invention.

In a second embodiment, shown in FIG. 2, the light source 120 may be un-collimated at the product end to illuminate larger products such as large meat samples or carcasses. The detection system of the second embodiment is more suited for applications where a larger region or area of the product is to be covered per scan.

The detector 110 employs an array of sensors to create fluorescence images of the fecal residue or other contaminant or substance on the meat or other product. In this alternative system, an individual pixel or a bin of pixels of the array sensors measure fluorescence signals.

A camera lens 115 is used to collect the emitted light from the product in response to excitation. The camera lens outputs an image signal which is divided into two or more channels, preferably using a beam splitter 116. The beam splitter 116 splits the image into two channels and focuses each signal onto one of two image sensors 117/118. It will be appreciated that in alternative embodiments the image signal may be divided into more than two channels associated with more than two image sensors and using more than one beam splitter, for example to detect more than one substance or contaminant in or on the illuminated product.

An optical filter before each image sensor filters the image to the appropriate waveband. The first image sensor 117 receives an image indicative of the waveband of the required base signal (625 nm-850 nm as in the preferred embodiment) and the second image sensor 118 receives an image indicative of the waveband of the fluorescence signal (666 nm to 676 nm).

In an alternative form of this embodiment, one image sensor can be used in conjunction with a filter wheel fitted with two or more optical filters. The image sensor would then sequentially receive the images within the various required wavebands as the filter wheel is rotated.

In yet another alternative form, the detector 110 can employ two image sensors each coupled with a camera lens and an optical filter to receive the images within the required wavebands. In this configuration, each sensor receives emitted light from the same region or spot of illumination through slightly different optical paths. Post image processing to fix the spatial offset can be employed in such a configuration.

In each optical configuration described above, preferably the detector 110 also obtains background images of the product. For this step, the excitation light is turned off briefly and each sensor 117/118 is allowed to receive background fluorescence/emissions. The background images are used in image processing to eliminate ambient light present in the detected images.

An image processing and control circuit board 119 may be used to control the illumination and reception of emitted light in accordance with this embodiment.

1.2 Signal Processing

Each of the first and second embodiments described above outputs a series of two or more filtered signals to a signal processing component of the system. The output signals include a base signal of a relatively wide waveband and one or more fluorescence signals of relatively narrow waveband(s). The waveband of the base signal contains the fluorescence wavelengths of each of the contaminants or substances to be detected, and the waveband of each fluorescence signal is a narrowband signal containing the fluorescence wavelength of the associated contaminant or substance. After receiving the filtered base and fluorescence signals, the signal processing component of the detector 110, processes the signal to determine the presence and absolute amounts of the contaminants or substance to be detected.

Figure 6:
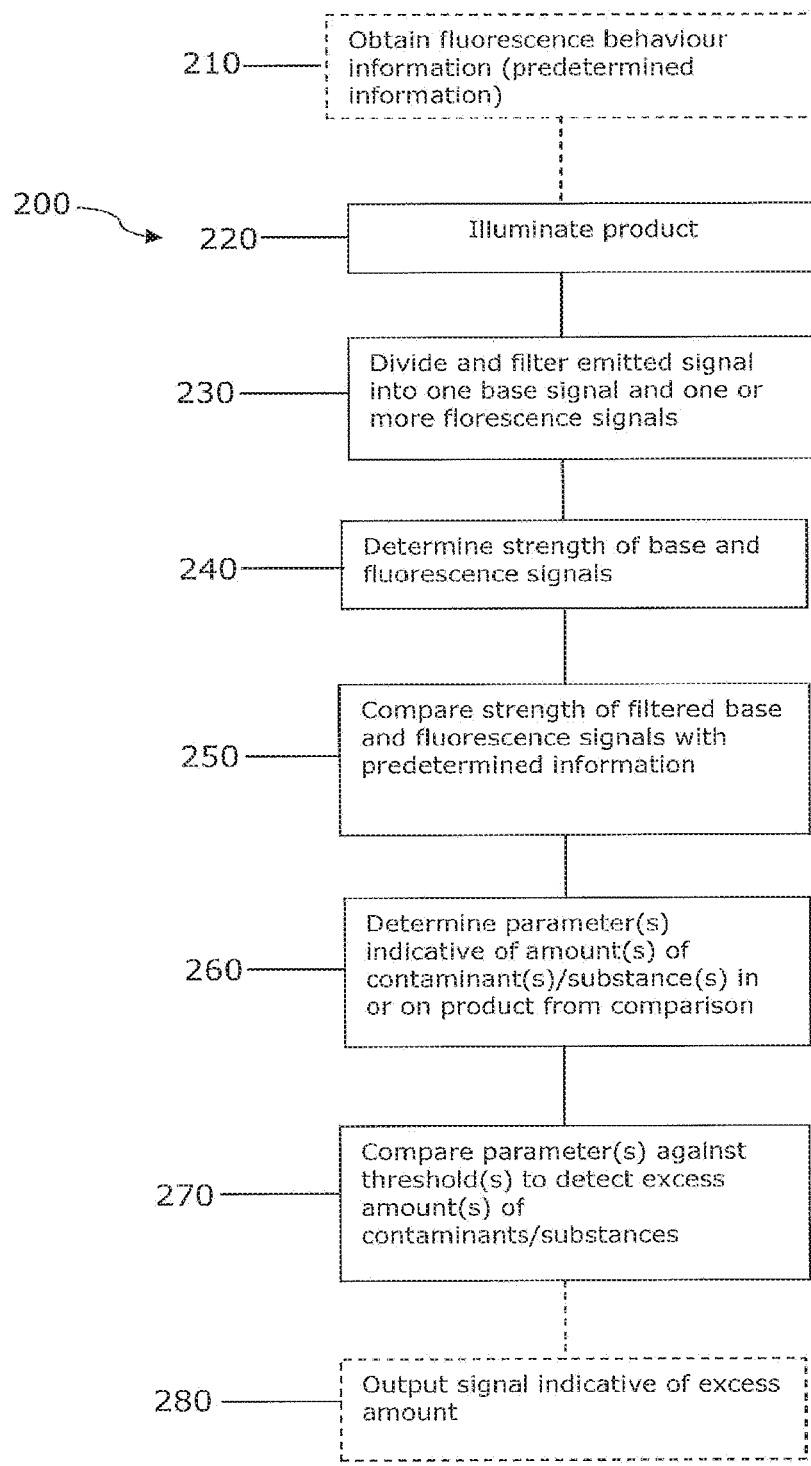
FIG. 6 is a flow diagram of a process of determining an absolute amount of a substance or contaminant in or on a product of the invention.
Figure 7:
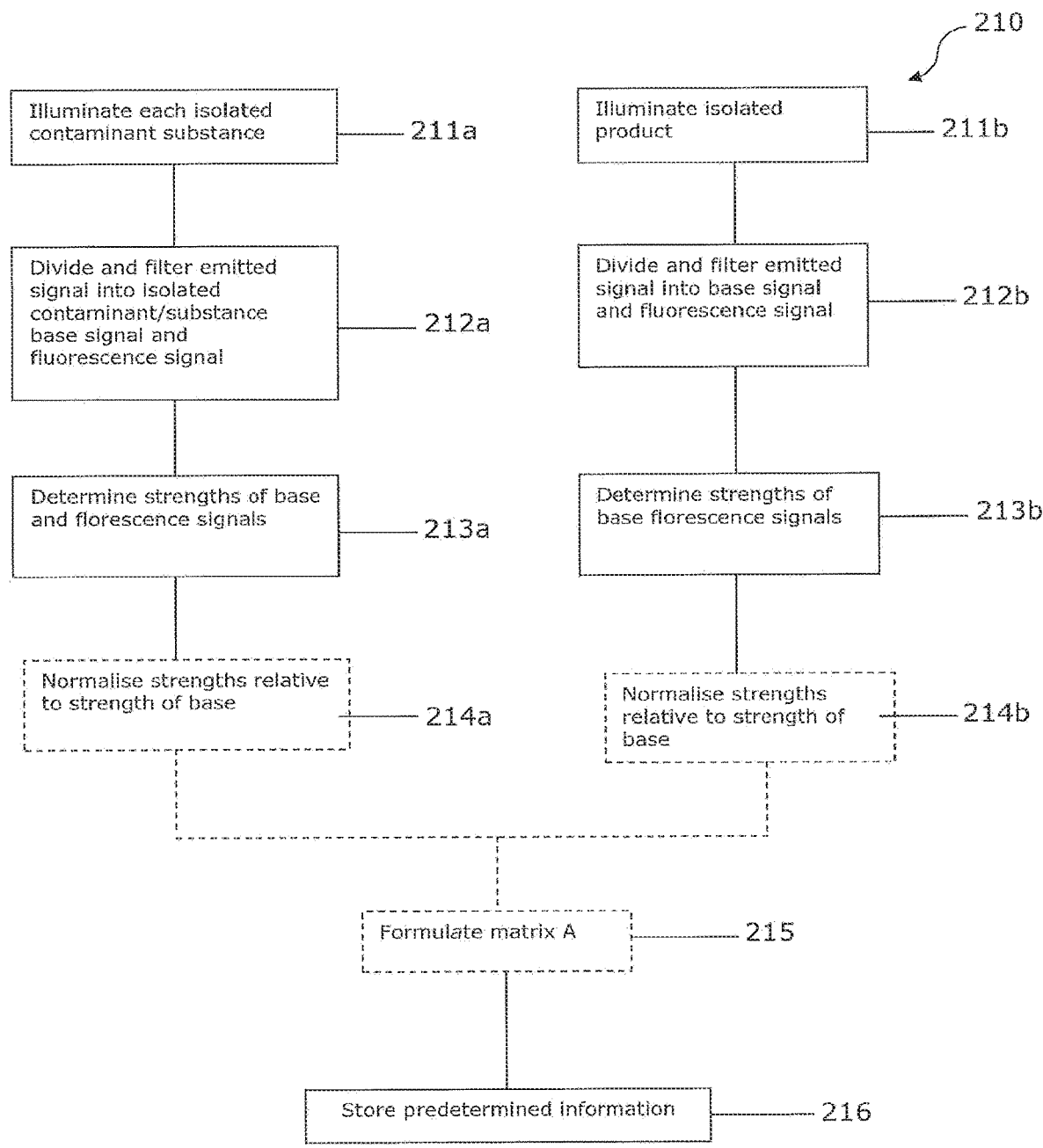
FIG. 7 is a flow diagram of a process of obtaining predetermined information in accordance with an initial step of FIG. 6.

Referring now to FIGS. 6 and 7, a process or method 200 for determining or predicting a value indicative of the absolute amount of the substance or contaminant in or on the product will now be described. The method is preferably achieved through the use of any one of the preferred systems described above in conjunction with the signal processing component of the system which is configured to process the data received from such systems. In particular, the signal processing component is configured to separate from the base signal of the product (with the substance or contaminant therein/thereon) a portion of the signal relating solely or predominantly to the substance or contaminant. This separation is done based on: the fluorescence signal, the fluorescence behaviour of the substance or contaminant in isolation from the product and/or the fluorescent behaviour of the product or a main substance of the product in isolation of the substance or contaminant.

At step 210, a memory component associated with the signal processing circuitry is initially populated with fluorescence behaviour information of at least the product or a main substance of the product, in isolation from the one or more contaminants or substances to be detected in or on the product, and the fluorescence behaviour of the one or more contaminants or substances in isolation of each other and in isolation of the product. The fluorescence behaviour information can be obtained using any one of the preferred systems described above. This step 210 is carried out initially for each product and contaminant/substance to be detected in or on the product to pre-calibrate the system for that product and contaminant(s)/substance(s). From there onwards, the system may be useable on a number of products in a production line for example to detect the presence of the contaminant(s)/substance(s) in or on the product. The system may be calibrated for a number of products and/or a number of contaminant(s)/substance(s) for each product at step 210.

Referring to FIG. 7 in particular, the fluorescence behaviour information is obtained 210 by:
- subjecting an isolated product or an isolated main substance of the product to excitation light 211b and obtaining from the emitted light a base signal and at least one fluorescence signal indicative of the light emitted across the wide base and narrow fluorescence wavebands respectively 212b; and
- subjecting each contaminant or substance (isolated from the product or the main substance of the product) to excitation light 211a and obtaining from the emitted light a base signal and at least a fluorescence signal indicative of the light emitted across the wide base and narrow fluorescence wavebands respectively 211b.

In the preferred embodiment, after obtaining the above signals, the following information is determined and data indicative of such information is stored in memory:
- at 213b the strength of the base signal associated with the isolated product (or main substance of the product) is calculated—$\text{Det1}_{IP}$,
- at 213b the strength of the fluorescence signal isolated associated with the isolated product (or main substance of the product) is also calculate—$\text{Det2}_{IP}$,
- at 213a, for each of the one or more isolated substances or contaminants, the strength of the base signal associated with the isolated substance or contaminant is calculated—$\text{Det1}_C$, and
- at 213a, for each of the one or more isolated substances or contaminants, the strength of the fluorescence signal isolated associated with the isolated contaminant or substance is also calculated—$\text{Det2}_C$, The strength may be calculated as an integral of the respective signal as shown in the following series of equations:

$$\text{Det1}_{IP} = \int_{BL}^{BU} F_{IP}(\lambda)d\lambda$$

$$\text{Det2}_{IP} = \int_{FL}^{FU} F_{IP}(\lambda)d\lambda$$

$$\text{Det1}_C = \int_{BL}^{BU} F_C(\lambda)d\lambda$$

$$\text{Det2}_C = \int_{FL}^{FU} F_C(\lambda)d\lambda$$

Where $F_{IP}(\lambda)$ and $F_C(\lambda)$ are the fluorescence waveform of isolated product and contaminant/substance respectively after excitation, BU is the upper wavelength of base signal, BL is the lower wavelength of the base signal, FU is the upper wavelength of the fluorescence signal and FL is the lower wavelength of the fluorescence signal.

For example, for the preferred embodiment of feces detection on meat described above, the predetermined information stored in memory is indicative of:

$$\text{Det1}_{meat} = \int_{625nm}^{850nm} F_{meat}(\lambda)d\lambda$$

$$\text{Det2}_{meat} = \int_{666nm}^{676nm} F_{meat}(\lambda)d\lambda$$

$$\text{Det1}_{feces} = \int_{625nm}^{850nm} F_{feces}(\lambda)d\lambda$$

$$\text{Det2}_{feces} = \int_{666nm}^{676nm} F_{feces}(\lambda)d\lambda$$

As will be explained further below, the strengths calculated at 213a and 213b may be normalised relative to the base signal strengths at 214a and 214b before being stored in memory. The absolute or normalised strength information or other data indicative thereof is stored in memory at 216.

Referring back to FIG. 6, during (preferably real time) product analysis, a product is first illuminated at step 220 and at step 230 the emitted signal in response to illumination is then divided into the base signal and the one or more fluorescence signals as described above. The signal processing component of the system receives the base and fluorescence signals and determines values indicative of the strength of each signal (step 240). The strengths are then compared to the predetermined information stored in memory at step 250 and from this comparison one or more parameters indicative of an amount of each substance/contaminant to be detected are calculated or predicted (step 260). From this determination or prediction the signal processing component may then preferably compare the parameter(s) against a threshold or thresholds to determine if the product contains an excess amount of the substance/contaminant (step 270) and preferably output a signal indicating such if the amount is in excess (step 280).

Two preferred methods are described below for determining or predicting a value indicative of the absolute amount of a contaminant or substance in or on a product from the comparison stage 250. Both methods operate to separate the portion of the emitted light that is due to the contaminant or substance by utilising the prior knowledge stored in memory.

1.2.1 First Preferred Method

In a first preferred embodiment the step of determining or predicting the value indicative of the amount of the substance or contaminant comprises multiplying the base signal and the fluorescence signal by the inverse of a matrix, A, containing the predetermined information described above. This matrix may be generated and pre-stored in memory at step 215 prior to product analysis or may be generated from pre-stored information during the comparison stage 250.

If a sample of interest contains x amount of uncontaminated product and y amount of contaminant or substance to be detected, the measured base and fluorescence signals, $Det1_P$ and $Det2_P$, are then linear combinations of the above equations as shown in equation 1.

$$Det1_{IP} \cdot x + Det1_C \cdot y = Det1_P$$

$$Det2_{IP} \cdot x + Det2_C \cdot y = Det2_P \quad \text{equation 1}$$

Matrix A is predetermined based on equation 1. The entities of the matrix A represent a collection of the above described predetermined information. The first column of the matrix represents isolated product normalized to the base signal of the isolated product. The second column represents isolated substance or contaminant normalized to the base signal of the isolated substance or contaminant.

This matrix A can be simplified further in terms of E which is defined as $$E = \frac{Det2}{Det1}.$$

For example, for determining one substance or contaminant in or on the product, matrix A can be expressed as:

$$A = \begin{bmatrix} \left(\frac{Det1}{Det1}\right)_{IP} & \left(\frac{Det1}{Det1}\right)_{C} \\ \left(\frac{Det2}{Det1}\right)_{IP} & \left(\frac{Det2}{Det1}\right)_{C} \end{bmatrix} = \begin{bmatrix} 1 & 1 \\ E_{IP} & E_C \end{bmatrix}$$

The products of $A^{-1}$ and any input matrices of the base and fluorescence signals of the product to be analysed, $$\begin{bmatrix} Det1_P \\ Det2_P \end{bmatrix}$$

will generate resultant matrices of $$\begin{bmatrix} I_P \\ I_C \end{bmatrix}$$

as shown in equation 3.

$$A^{-1} \times \begin{bmatrix} Det1_P \\ Det2_P \end{bmatrix} = \begin{bmatrix} x \\ y \end{bmatrix} = \begin{bmatrix} I_P \\ I_C \end{bmatrix} \quad \text{equation 3}$$

The entities of the resultant matrices, $I_P$ and $I_C$ represent calculated absolute intensities of the product and of the contaminant/substance respectively.

The matrix A may be an n by n or m by n sized matrix, where n and m depend on the number of substances or contaminants to be determined. For example A may be 4×4 matrix determined from a 1×4 input matrix of signal strengths. However the size of the input matrix does not exclusively represent the number of detectors. In this example, two detectors still can be used under different experimental conditions to construct the input matrix such as at two different excitation wavelengths, two different excitation powers or two different detection time frames.

1.2.2 Second Preferred Method

In an alternative embodiment the step of determined or predicting the value indicative of the amount of the substance or contaminant comprises determining a parameter, $R_C$, indicative of the deviation between the signals associated with the product from the signals associated with the isolated product. In particular, $R_c$ is determined from the difference between the normalised strength of the product fluorescence signal and the normalised strength of the isolated product fluorescence signal.

A parameter, $R_C$ is determined in this method based on equation 4 below.

$$R_C = \left(\left(\frac{Det2}{Det1}\right)_P - \left(\frac{Det2}{Det1}\right)_{IP}\right) \times Det2_P$$

$R_C$ is a parameter indicative of the absolute strength of the emitted light signal due to the associate contaminant or substance.

1.2.3 Determining Excess Amount of Contaminant or Substance

In addition to determining or calculating the above two parameters, $I_C$ and $R_C$, the signal processing system may be further configured to determine or predict if there is an excess amount of the contaminant or substance in the product from one or both parameters.

The signal processing system may be configured to compare one or each parameter against a predetermined threshold associated with the parameter and indicates an excess amount of substance or contaminant when one or both parameters exceed the associated threshold. Alternatively, the parameters may be combined, for example summed or multiplied, and their combination is compared against a predetermined threshold to indicate excess amount of substance or contaminant.

It is noted that the embodiments described above may be described as a process that is depicted as a flowchart or a flow diagram, a structure diagram. Although a flowchart may describe the operations as a sequential process, many of the operations can be performed in parallel or concurrently. In addition, the order of the operations may be rearranged. A process is terminated when its operations are completed. A process may correspond to a method, a function, a procedure, a subroutine, a subprogram, etc., in a computer program. When a process corresponds to a function, its termination corresponds to a return of the function to the calling function or a main function.

In the foregoing, a storage medium may represent one or more devices for storing data, including read-only memory (ROM), random access memory (RAM), magnetic disk storage mediums, optical storage mediums, flash memory devices and/or other machine readable mediums for storing information. The terms "machine readable medium" and "computer readable medium" include, but are not limited to portable or fixed storage devices, optical storage devices, and/or various other mediums capable of storing, containing or carrying instruction(s) and/or data.

The various illustrative logical blocks, modules, circuits, elements, and/or components described in connection with the examples disclosed herein may be implemented or performed with any combination of one or more of the following implementation mediums: general purpose processor, a digital signal processor (DSP), an application specific integrated circuit (ASIC), a field programmable gate array (FPGA) or other programmable logic component, discrete gate or transistor logic, discrete hardware components, designed to perform the one or more functions described herein. To perform the various functions and transfer information between the blocks, modules, circuits, elements and/or components described, the implementation mediums may be communicatively coupled either directly or via any suitable communications network as is well known in the arts of electrical and software engineering. A general purpose processor may be a microprocessor, but in the alternative, the processor may be any conventional processor, controller, microcontroller, circuit, and/or state machine. A processor may also be implemented as a combination of computing components, e.g., a combination of a DSP and a microprocessor, a number of microprocessors, one or more microprocessors in conjunction with a DSP core, or any other such configuration.

One or more of the components and functions illustrated the figures may be rearranged and/or combined into a single component or embodied in several components without departing from the invention. Additional elements or components may also be added without departing from the invention.

In its various aspects, the invention can be embodied in a computer-implemented process, a machine (such as an electronic device, or a general purpose computer or other device that provides a platform on which computer programs can be executed), processes performed by these machines, or an article of manufacture. Such articles can include a computer program product or digital information product in which a computer readable storage medium containing computer program instructions or computer readable data stored thereon, and processes and machines that create and use these articles of manufacture.

2. Experimentation

Experimentation was conducted to verify the utility of the invention in the application of determination of fecal contamination in meat products.

Figure 3A:
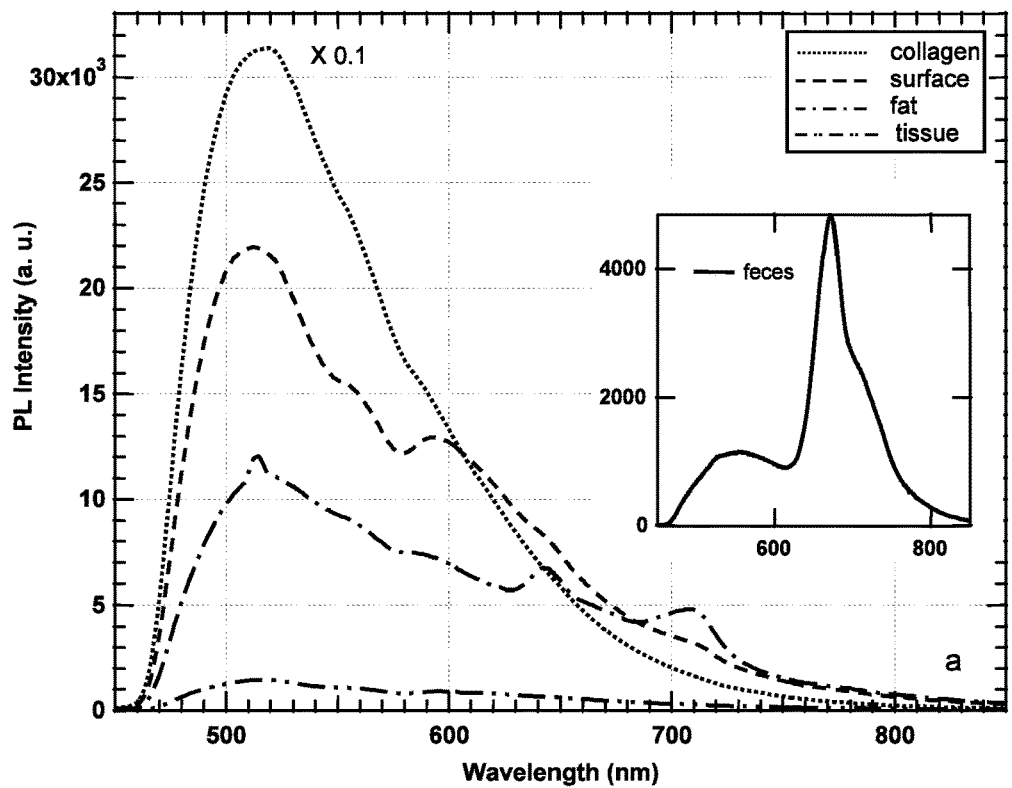
FIG. 3A is a graph showing collagen (re-scaled due to high intensity), fat, surface and tissue fluorescence spectra under 450 nm excitation, with diluted feces fluorescence spectra shown as an inset.
Figure 3B:
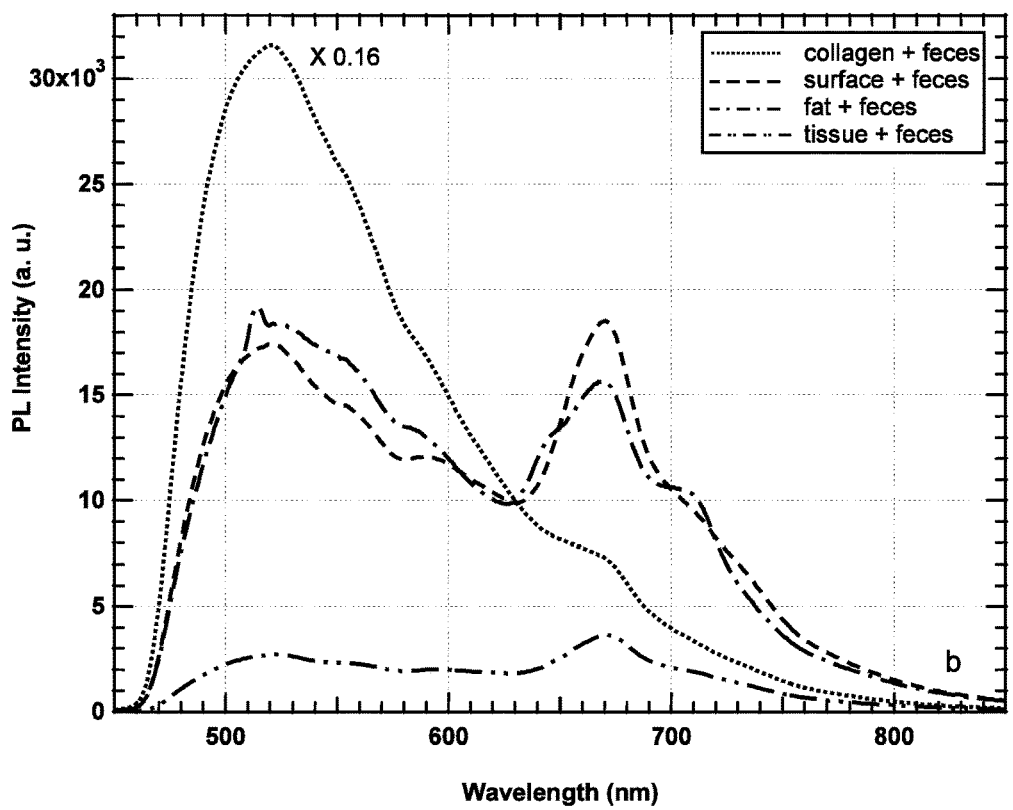
FIG. 3B is a graph showing fluorescence spectra of the same meat samples contaminated with feces.

FIG. 3A shows fluorescence of isolated collagen, surface, fat and tissue within lamb spare flap cuts. Fluorescence of diluted sheep feces is also presented on the inset of FIG. 3A. Small volume (0.1 ml) of diluted feces were deposited to the same excitation spot of each sample and the resultant spectra were taken immediately after as shown in FIG. 3B.

Among the investigated meat samples collagen showed the highest fluorescence intensity while tissue showed the minimum. In general meat fluorescence is similar in that the peak wavelength is around 520 nm, under 450 nm excitation, and that the fluorescence shape is asymmetric with respect to wavelengths. Two dips also seen at 545 nm and 576 nm are believed to be re-absorption of oxygenated hemoglobin. Due to relatively small meat fluorescence and high blood vessel content, tissue showed distinctive hemoglobin absorptions while the least hemoglobin absorption was found in collagen. Unlike the other samples fat fluorescence also showed narrow fluorescence peaks of porphyrin between 630 nm and 730 nm.

It should be noted that tissue showed the greatest contrast between contaminated and uncontaminated fluorescence signature at 670 nm. On the other hand collagen showed very little change at the same spectral region even though the same volume of feces was applied. In other words relative signal of feces on collagen is very small compared to that in other meat parts. This could result in false negative detection. Hence it is essential to evaluate absolute fluorescence signal of chlorophyll rather than relative signal to minimize false detection.

For this purpose we have developed a method of using two detection parameters, $I_{feces}$ and $R_{feces}$.

The first detection parameter $I_{feces}$ was calculated from an inverse matrix problem solving method.

Figure 4:
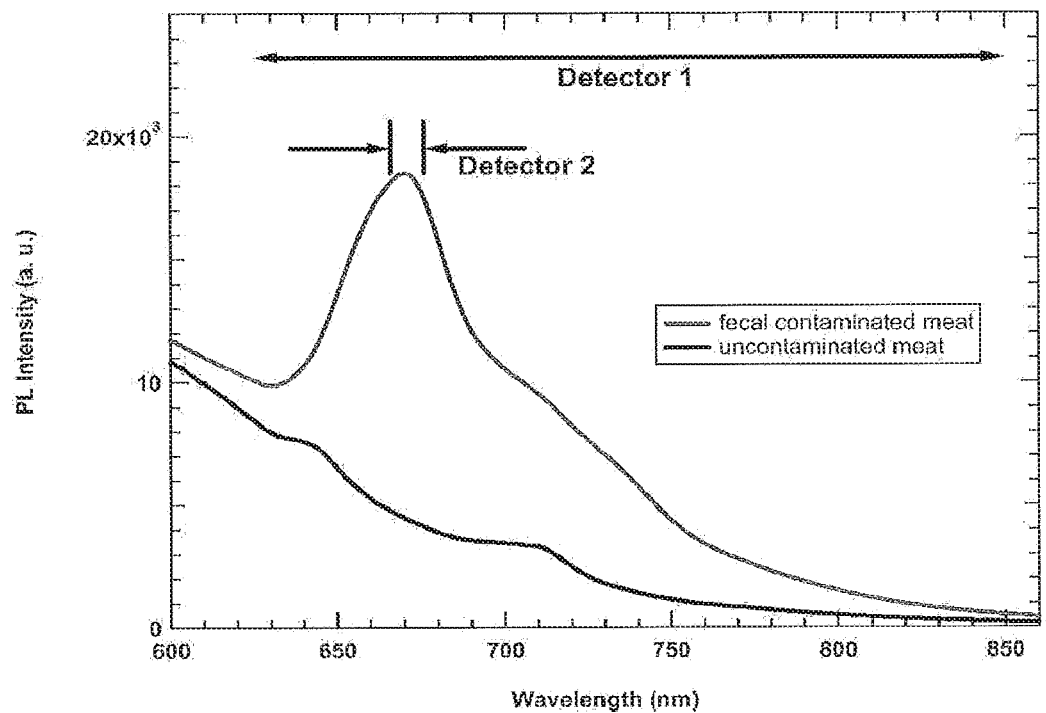
FIG. 4 is a graph showing fluorescence of chlorophyll present on the surface/epimysium of meat.

As shown in FIG. 4 each detector (113 of FIG. 1 is detector 1 and 114 of FIG. 1 is detector 2 for example) receives fluorescence signal equivalent to the area under the curve provided by the optical filter if detector response with wavelength is ignored. Signal strength received by each detector from each isolated meat and fecal solution can be expressed as $$Det1_{meat} = \int_{625nm}^{850nm} F_{meat}(\lambda)d\lambda$$

$$Det2_{meat} = \int_{666nm}^{676nm} F_{meat}(\lambda)d\lambda$$

$$Det1_{feces} = \int_{625nm}^{850nm} F_{feces}(\lambda)d\lambda$$

$$Det2_{feces} = \int_{666nm}^{676nm} F_{feces}(\lambda)d\lambda,$$

where $F_{meat}(\lambda)$ and $F_{feces}(\lambda)$ are the fluorescence waveform of isolated meat and fecal solution, respectively.

To calculate the parameter $I_{feces}$ a 2×2 matrix A was predetermined based on equation 1. The entities of the matrix A represent a collection of uncontaminated collagen and diluted feces signals each measured by detector 1 and detector 2 simultaneously. The first column of the matrix represents uncontaminated collagen normalized to detector 1. The second column represents diluted feces normalized to detector 1 value. It should be noted that we have used detector values measured from isolated collagen to represent uncontaminated meat. Due to the high collagen fluorescence signal compared to fecal signal, it was a good set point to test sensitivity of the inverse matrix problem solving method.

This matrix A can be simplified further in terms of E which is defined as $$E = \frac{\text{Det2}}{\text{Det1}}.$$

$$A = \begin{bmatrix} \left(\frac{\text{Det1}}{\text{Det1}}\right)_{collagen} & \left(\frac{\text{Det1}}{\text{Det1}}\right)_{feces} \\ \left(\frac{\text{Det2}}{\text{Det1}}\right)_{collagen} & \left(\frac{\text{Det2}}{\text{Det1}}\right)_{feces} \end{bmatrix} = \begin{bmatrix} 1 & 1 \\ E_{collagen} & E_{feces} \end{bmatrix}$$

The products of $A^{-1}$ and any input matrices of sample signal, $$\begin{bmatrix} \text{Det1}_{sample} \\ \text{Det2}_{sample} \end{bmatrix}$$

will generate resultant matrices of $$\begin{bmatrix} I_{meat} \\ I_{feces} \end{bmatrix}.$$

$$A^{-1} \times \begin{bmatrix} \text{Det1}_{sample} \\ \text{Det2}_{sample} \end{bmatrix} = \begin{bmatrix} x \\ y \end{bmatrix} = \begin{bmatrix} I_{meat} \\ I_{feces} \end{bmatrix}$$

The entities of the resultant matrices, $I_{meat}$ and $I_{feces}$ represent calculated absolute intensities of meat background and fecal contamination respectively.

For fecal detection $I_{feces}$ has been considered in the signal processing. The entity $I_{meat}$ is also a valid parameter for estimation of uncontaminated meat within the sample of interest.

The 2×2 matrix can be expanded to n×n or m×n, where n and m can be any integer. Having bigger matrix sizes means that we can quantify more fluorescing material within the sample of interest such as fecal residue, collagen, fat and porphyrin.

The inverse matrix solving method can therefore be applied in more generalized situations where fuller analysis is needed.

The second parameter $R_{feces}$ was calculated from differences between the ratio of measured data and the ratio of uncontaminated collagen. The parameter $R_{feces}$ is defined in equation 3.

$$R_{feces} = \left(\left(\frac{\text{Det2}}{\text{Det1}}\right)_{sample} - \left(\frac{\text{Det2}}{\text{Det1}}\right)_{collagen}\right) \times \text{Det2}_{sample}$$

The first term is the measured data from any sample of interest expressed as a ratio of the two detectors. The second term in equation 3 is predetermined ratio of uncontaminated collagen. The difference between the first and the second term is then multiplied to measured detector 2 signal of the same sample to yield an absolute calculated fecal fluorescence signal.

Figure 5:
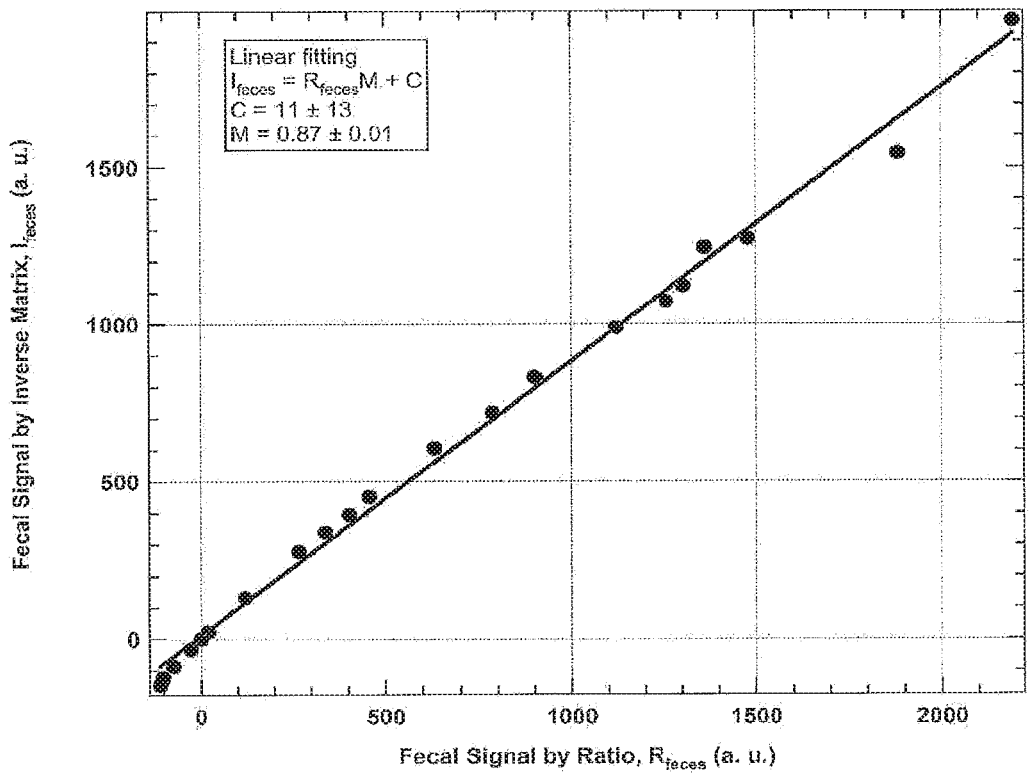
FIG. 5 is a graph showing comparison of the two parameters, $R_{feces}$ and $I_{feces}$, in the possible ranges of both positive and negative fecal detection.

The two parameters $I_{feces}$ and $R_{feces}$ gave independent estimations of fecal fluorescence strength. The values of $I_{feces}$ and $R_{feces}$ calculated from contaminated and uncontaminated meat samples showed a good agreement as shown in FIG. 5.

An arbitrary threshold level for fecal detection was set at 50. Any value above this level is considered as fecal contamination. The threshold level can be varied.

In a signal processing loop the values of $I_{feces}$ and $R_{feces}$ are compared to the predetermined threshold level and a warning indication is generated when the values of the both parameters exceed the threshold.

The fecal contamination detection limit is approximately equal to 1/32 dilution of feces with water. Since collimated beam was used as a primary excitation delivery, the detection performance with distance was stable from 100 mm to 400 mm from the surface of meat samples.

The foregoing description of the invention includes preferred forms thereof. Modifications may be made thereto without departing from the scope of the invention as defined in the accompanying claims.

The invention claimed is:

1. A method for determining an amount of a substance or contaminant in or on each of a series of illuminated products emitting differing levels of light intensity when illuminated, the method comprising the steps of for each product:
   receiving a first signal indicative of intensity of light emitted from the product across a first waveband said first waveband containing one or more wavelengths of highest intensity associated with fluorescent properties of the substance or contaminant to be detected and containing a wider band of other wavelengths emitted from the product,
   receiving a second signal indicative of intensity of light emitted from the product across a second waveband, said second waveband narrower than the first waveband, said second waveband within the first waveband, and said second waveband containing one or more wavelengths of highest intensity associated with fluorescent properties of the substance or contaminant to be detected,
   determining or predicting a value indicative of the amount of the substance or contaminant in or on the product, from a strength of the first signal and a strength of the second signal and from predetermined information relating to fluorescence behaviour of a same or similar product or a main substance of the product isolated from the substance or contaminant (hereinafter referred to as isolated product) and/or relating to fluorescence behaviour of the substance or contaminant isolated from the product, by separating from the first signal a portion of signal strength relating to the substance or contaminant based on the second signal strength, the fluorescent behaviour of the substance or contaminant in isolation from the product, and the fluorescent behaviour of the isolated product, wherein each product is a meat sample or carcass, and the main substance of the product is any of or any combination of collagen, tissue and fat, and the substance(s) or contaminant(s) to be determined is any of or any combination of fecal residue, fat, porphyrin, collagen and bacteria.

2. The method as claimed in claim 1 wherein the predetermined information relates to:

strengths of first and second isolated product signals indicative of the light emitted from the isolated product across the first and second wavebands respectively in response to optical excitation, and strengths of first and second isolated substance or contaminant signals indicative of the light emitted from the isolated substance or contaminant within the first and second wavebands respectively in response to optical excitation.

3. The method as claimed in claim 2 wherein the predetermined information includes one or more of:

a normalised strength of the first and/or second isolated product signal relative to the first isolated product signal, and a normalised strength of the first and/or second isolated substance or contaminant signal relative to the first isolated substance or contaminant signal, for each of the isolated substances or contaminants.

4. The method as claimed in claim 1 wherein the strength of the isolated product signal is an integral of an intensity of the isolated product signal across the relevant waveband, and the strength of the isolated substance or contaminant signal is an integral of an intensity of the isolated substance or contaminant signal across the relevant waveband.

5. The method as claimed in claim 1 wherein determining or predicting the value indicative of the amount of the substance or contaminant comprises multiplying the first signal and the second signal by an inverse of a matrix containing the strength of each of the first and second isolated product signals and the strength of each of the first and second isolated substance or contaminant signals, for each of substance or contaminants.

6. The method as claimed in claim 1 further comprising, prior to receiving the first and second signals, the steps of:

illuminating the product with light at an excitation wavelength outside the first and second wavebands, receiving light emitted from the product in response to the illuminating, and filtering the emitted light into first and second filtered light signals within the first and second wavebands respectively.

7. The method as claimed in claim 1 further comprising the step of deriving the predetermined information.

8. The method as claimed in claim 7 wherein the step of deriving the predetermined information comprises:

obtaining first and second isolated product signals, obtaining for each of the substances or contaminants, first and second isolated substance or contaminant signal.

9. The method as claimed in claim 8 wherein the step of obtaining the first and second isolated product signals comprises:

illuminating the isolated product with light at an excitation wavelength outside the first and second wavebands, receiving light emitted from the product in response to the illuminating, and filtering the emitted light into first and second filtered light signals within the first and second wavebands respectively.

10. The method as claimed in claim 8 wherein the step of obtaining the first and second isolated substance or contaminant signals comprises:

illuminating the isolated substance or contaminant with light at an excitation wavelength outside the first and second wavebands, receiving light emitted from the substance or contaminant in response to the illumination, and filtering the emitted light into first and second filtered light signals within the first and second wavebands respectively.

11. The method as claimed in claim 1 also comprising determining an amount of a further substance or contaminant in or on the product, by:

receiving a further signal indicative of intensity of light emitted from the product across a further waveband within the first waveband, both the first waveband and the further waveband containing one or more wavelengths associate with the fluorescent properties of the further substance or contaminant, determining or predicting a value indicative of an amount of the further substance or contaminant from a strength of the first signal and a strength of the further signal and from predetermined information relating to fluorescence behaviour of the isolated product and/or relating to the fluorescence behaviour of the further substance or contaminant isolated from the product, by separating from the first signal a portion of signal strength relating to the further substance or contaminant based on the further signal strength, the fluorescent behaviour of the further substance or contaminant in isolation from the product, and the fluorescent behaviour of the isolated product, wherein the further substance(s) or contaminant(s) is any of or any combination of fecal residue, fat porphyrin, collagen and bacteria.

* * * * *